United States Patent [19]

Han

[11] Patent Number: 4,888,357
[45] Date of Patent: Dec. 19, 1989

[54] ANTIARTHRITIC β-CYCLOALKYL-β-OXOPROPIONITRILES

[75] Inventor: William T. Han, Cheshire, Conn.

[73] Assignee: Bristol-Myers Company, New York, N.Y.

[21] Appl. No.: 148,540

[22] Filed: Jan. 26, 1988

[51] Int. Cl.$^4$ .................... A61K 31/275; C07C 121/46
[52] U.S. Cl. ..................................... 514/519; 558/430; 558/432; 558/433; 558/434
[58] Field of Search ................ 514/519; 558/434, 433, 558/432, 430

[56] References Cited

U.S. PATENT DOCUMENTS

| | | | |
|---|---|---|---|
| 3,016,295 | 1/1962 | Davidson et al. | 71/105 |
| 3,406,183 | 10/1968 | Laliberte | 260/326.5 |
| 4,061,767 | 12/1977 | Ertel et al. | 424/282 |
| 4,170,656 | 10/1979 | Hanifin, Jr. et al. | 424/304 |
| 4,173,650 | 11/1979 | Hanifin, Jr. et al. | 548/247 X |
| 4,189,436 | 2/1980 | Hanifin et al. | 549/72 |
| 4,197,310 | 4/1980 | Hanifin, Jr. et al. | 549/72 X |
| 4,254,047 | 3/1981 | Hanifin, Jr. et al. | 548/248 X |
| 4,254,048 | 3/1981 | Hanifin, Jr. et al. | 424/304 X |
| 4,254,049 | 3/1981 | Hanifin, Jr. et al. | 548/248 X |
| 4,256,759 | 3/1981 | Walker | 548/248 X |
| 4,435,407 | 5/1984 | Walker | 546/281 X |
| 4,644,010 | 2/1987 | Walker | 514/423 |

FOREIGN PATENT DOCUMENTS

| | | |
|---|---|---|
| 2555789 | 7/1977 | Fed. Rep. of Germany . |
| 3217446 | 11/1983 | Fed. Rep. of Germany . |
| 1112210 | 5/1968 | United Kingdom . |

OTHER PUBLICATIONS

J. Med. Chem., 1979, 22:1385–9; Ridge, et al.
Chem. Abst. (1929), 23:4193; Pabst.

Primary Examiner—Joseph Paul Brust
Attorney, Agent, or Firm—Mollie M. Yang

[57] ABSTRACT

Disclosed herein are novel β-cycloalkyl-β-oxopropionitriles which exhibit anti-inflammatory/antiarthritic activities.

19 Claims, No Drawings

ANTIARTHRITIC β-CYCLOALKYL-β-OXOPROPIONITRILES

BACKGROUND OF THE INVENTION

1. Field of the Invention

The present invention relates to a β-oxo-propionitriles active as anti-inflammatory and anti-arthritic agents, to their use in the treatmen of inflammatory or arthritic conditions, and to pharmaceutical compositions containing the novel compounds.

2. Description of Related Art

Benzoylacetonitrile (I) and its monofluoro analogues have been found to be effective inhibitors of adjuvant-induced arthritis in rats (J. Med. Chem., 1979, 22:1385-9). The same article, as well as U.S. Pat. No.4,189,436, also discloses β-oxo-β-thiophenepropionitriles (II) as anti-arthritic agents.

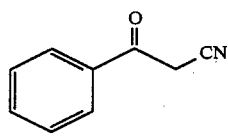

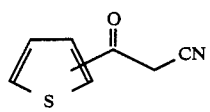

β-Oxopropionitriles having an α-carbonyl or thiocarbonyl substituent are reported as anti-inflammatory and/or anti-arthritic agents in (a) through (e):

(a) U.S. Pat. No. 4,061,767 and German Offenlegungsschrif No. 2,555,789 disclose, resectively, 2-hydroxyethylidenecyanoacetic acid anilide derivatives of formulas (IIIa) and (IIIb), wherein Ar is inter alia mono-, di-, or tri-substituted phenyl, said substituent may be, for example, halogen, alkyl, alkoxy, or halo-substituted alkyl.

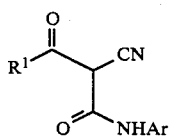

a: $R^1$ = methyl
b: $R^1$ = H, benzyl, $C_{2-17}$ alkyl (b) U.S. Pat. Nos. 4,254,047, 4,254,048, 4,254,049, 4,170,656, and 4,173,650 disclose a group of compounds that may be represented by the generic structure (IV) wherein X is oxygen, sulfur, methylene, or a direct bond; Ar is phenyl opt. substituted with one or more of the same of different groups selected from halogen, alkyl, alkoxy, trifluoromethyl, and trichloromethyl.

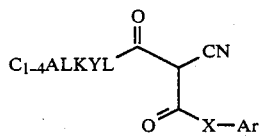

(c) U.S. Pat. No. 4,197,310 discloses thiophenepropionitriles of formula (V) wherein R is hydrogen, lower alkyl, or halogen.

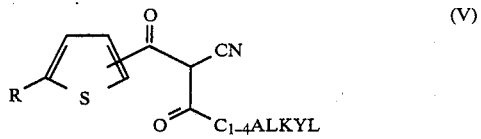

(d) U.S. Pat. Nos. 4,256,759, 4,644,010 and 4,435,407 disclose β-oxo-β-carbamoylpyrrolepropionitriles encompassed by generic formula (VI) where $R^1$ is H or alkyl; $R^2$ and $R^3$ are independently H or alkyl; and $R^4$ is phenyl or a heterocyclic radical both of which may be opt. substituted with alkyl, alkoxy, hydroxy, halogen, or trifluoromethyl.

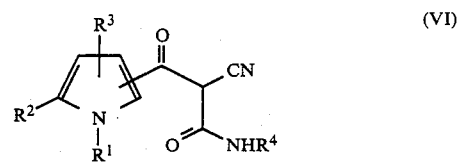

(e) German Offenlegungsschrift No. 3,217,446 discloses thiocarbamoyl-thenoylacetonitriles of formula (VII) wherein $R^1$ is H, halogen, alkyl, or alkoxy; $R^2$ is $C_{3-6}$cycloalkyl, benzyl, furfuryl, or phenyl opt. substituted with halogen alkyl, alkoxy, alkyllthio, or tribluoromethyl.

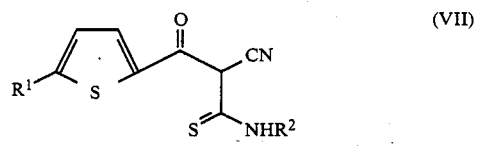

(f) British Patent 1,112,210 discloses 2-cyanomalonic acid thioamide derivatives of formula (VIII) wherein $R^1$ is inter alia alkyl or aralkyl; $R^2$ is H, alkyl, or aryl; and $R^3$ is alkyl or aralkyl.

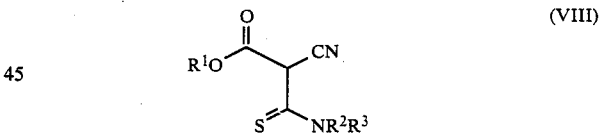

These compounds are said to be useful as bactericides, fungicides, and diuretics. No anti-inflammatory or anti-arthritic acivities are disclosed.

(g) The preparation of 3-cyanopentane-2,4-dione from cyanogen and acetylacetone was reported in Berichte, 1898, 31:2944; however, no biological property was disclosed.

Compounds of the present invention may be distinguished over compounds disclosed in items (a)–(g) above by the presence of both the β-cycloalkyl group, and the β-aliphatic substituted carbamoyl group or the α-alkanoyl group.

A list of additional references disclosing compounds having the α-carbonyl-β-oxopropionitrile fragment is given below; however, the compounds described therein are not ketonitriles and have not been reported as anti-inflammatory or anti-arthritic agents.

(h) U.S. Paten 3,406,183 discloses 3-N-arylamino-3-mercapo-2-cyano-acrylamides of the formula (IX) wherein $R^1$ is H and $R^2$ is alkyl or phenyl; or $R^1$ and $R^2$ together represent -(CH$_2$)$_{4-5}$-; and Ar is opt. substituted phenyl.

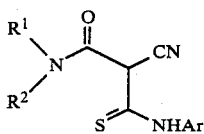

(IX)

These compounds are alleged to be useful as anhelmintic and antibacterial agents.

(i) Pabst (Arch. Pharm., 1929, 267:325-52) reported the preparation of a series of 2-cyanomalonamic acid esters and amides, for example, (X) and (XI).

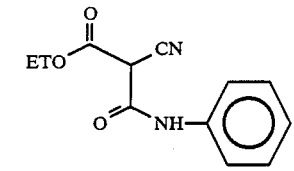

(X)

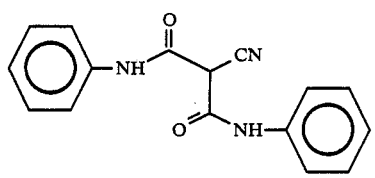

(XI)

(j) U.S. Pat. No. 3,016,295 discloses 2-cyanomalonamic acid ester derivatives having formula (XII) wherein $R^2$ is alkyl or alkyl-(OCH$_2$CH$_2$-)$_{1-2}$ and $R^2$ is H or alkyl.

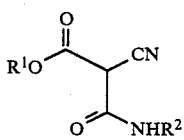

(XII)

These compounds are said to be useful in altering growth characteristics of plants.

SUMMARY OF INVENTION

The present invention provides compounds having the formula (XIII)

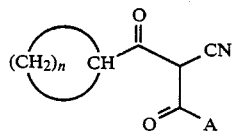

(XIII)

wherein
n=2, 3, 4, or 5;
A is selected from the group consisting of C$_{1-5}$alkyl, NHR$^1$, and NR$^2$R$^3$ wherein R$^1$ is selected from the group consisting of C$_{1-5}$alkyl, C$_{2-5}$alkenyl, C$_{2-5}$alkynyl, and C$_{3-6}$cycloalkyl with the proviso that when n is 2, R$^1$ is not ethyl or isopropyl; R$^2$ and R$^3$ are same or different C$_{1-5}$alkyl;
or a pharmaceutically acceptable salt thereof.

A preferred embodiment provides compounds of formula (XIII) wherein n is 2 or 3, with n=2 being the most preferred.

A further preferred embodiment provides compounds of formula (XIII) wherein A is C$_{1-5}$alkyl, di(C$_{1-5}$alkyl)amino, or NHR$^1$ wherein R$^1$ is selected from the group consisting of methyl, C$_{4-5}$ alkyl, C$_{3-5}$ alkenyl, C$_{3-5}$ alkynyl, or C$_{3-4}$ cycloalkyl with methyl being the most preferred R$^1$.

A further aspect of the present invention provides a pharmaceutical composition which comprises an anti-inflammatory or an anti-arthritic effective amount of a compound of formula (XIII) and a pharmaceutically acceptable carrier.

Yet a further aspect of the present invention provides a method for treating a mammalian host afflicted with an inflammatory or arthritic condition which comprises administering to said host an anti-inflammatory or anti-arthritic effective amount of a compound of formula (XIII).

DETAILED DESCRIPTION OF THE INVENTION

As used herein, the term "alkyl" includes straight nd branched carbon chain.

Compounds of the present invention may exist in equilibrium with the enol form (XIIIa); however, for the sake of uniformity and convenience, the compounds are depicted as the keto form throughout the specification. It will be appreciated that the tautomeric hydrogen is sufficiently acidic to form salts with pharmaceutically acceptable inorganic or organic bases such as alkali metal or alkaline earth metal hydroxides; ammonia; mono-, di-, or trialkylamines; heterocyclic amines; or mono-, di-, or ri(hydroxyethyl)amines; these salts are also within the scope of this invention.

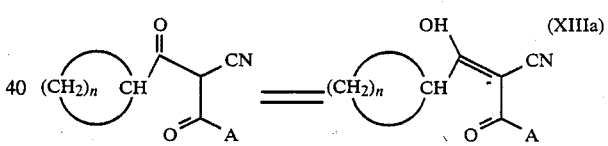

(XIIIa)

The α-carbamoyl- or α-alkanoyl-β-oxopropionitriles of the present invention may be prepared by methods known in the literature; in particular by (1) base-catalyzed ring opening of the appropriately substituted isoxazole; or (2) reacting a β-oxopropionitrile with an isocyanate to provide the α-carbamoyl compound, or with an acid halide to provide the corresponding α-alkanoyl derivative.

Scheme 1 shows the reacion steps for the preparaaion of isoxazole-4-carboxamides and the subsequent ring opening to provide the corresponding α-carbamoyl-β-oxopropionitrile product.

Scheme 1

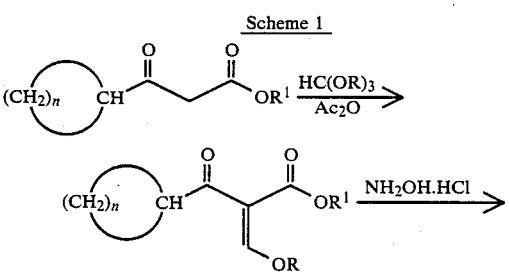

-continued
Scheme 1

Scheme 2

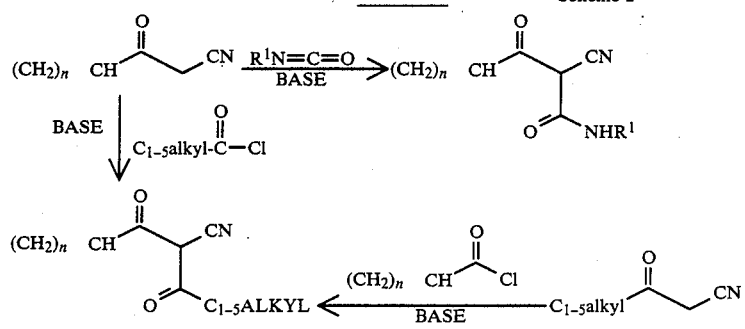

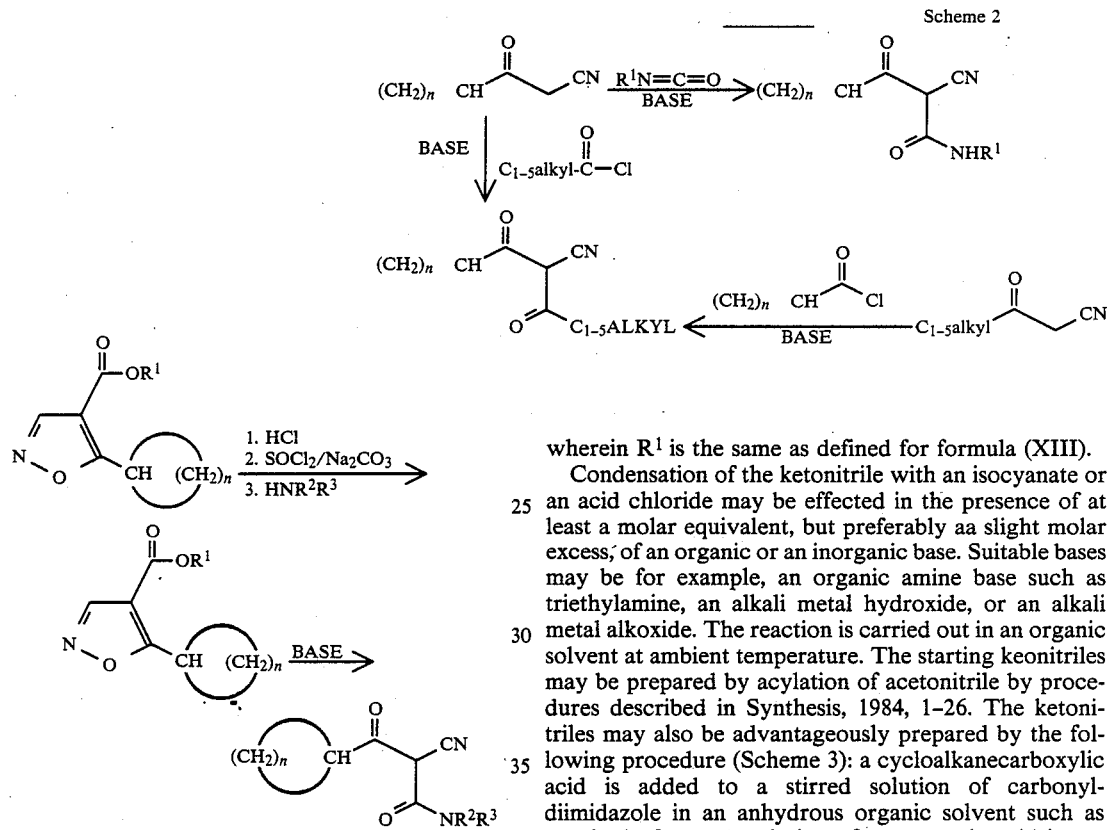

wherein $R^1$ is the same as defined for formula (XIII).

Condensation of the ketonitrile with an isocyanate or an acid chloride may be effected in the presence of at least a molar equivalent, but preferably aa slight molar excess, of an organic or an inorganic base. Suitable bases may be for example, an organic amine base such as triethylamine, an alkali metal hydroxide, or an alkali metal alkoxide. The reaction is carried out in an organic solvent at ambient temperature. The starting keonitriles may be prepared by acylation of acetonitrile by procedures described in Synthesis, 1984, 1-26. The ketonitriles may also be advantageously prepared by the following procedure (Scheme 3): a cycloalkanecarboxylic acid is added to a stirred solution of carbonyldiimidazole in an anhydrous organic solvent such as tetrahydrofuran. A solution of cyanoacetic acid in organic solvent is treated with a strong base, e.g. Grignard reagent such as isopropyl magnesium chloride. The mixture is stirred for several hours, and to it is added, dropwise, the previously prepared carbonyl imidazolide solution. After several hours of stirring, the reaction is quenched by addition of acid. The solution is extracted with an appropriate organic solvent such as ethyl acetate or ether, washed, and further purified by chromatography to give pure ketonitrile product.

wherein R and $R^1$ are independently a lower alkyl group; $R^2$ is H and $R^3$ is selected from the group consisting of $C_{1-5}$alkyl, $C_{1-5}$alklenyl, $C_{2-5}$alkynyl, and $C_{3-6}$cycloalkyl; or $R^2$ and $R^3$ are same or different $C_{1-5}$alkyl.

The starting material β-cycloalkyl-β-oxopropionate (prepared by the procedure described in J. Am. Chem. Soc., 1948, 70:497) is heated with an excess of an trialkyl orthoformate such as riethyl orthoformate in an acid anhydride usch as cetic anhydride, preferably to the refluxing temperature of the reaction mixture, for several hours. The resultan enol eher is treated with at least an equimolar amount of hydroxylamine in an organic solvent such as ethanol at elevated temperature, preferably refluxing temperature of the reaction mixture, to provide the isoxazole carboxylate. The carboxylate is converted to the amide by conventional method involving the hydrolysis of the ester group under acidic conditions, reacting the resultant carboxylic acid with thionyl chloride, and finally treating the acid chloride with the appropriate amine. The amine may serve as the hydrogen chloride acceptor if at least two molar equivalents are used; alternatively, a tertiary amine such as diisopropylethylamine may be used for that purpose. Treatment of the isoxazole carboxamide with a basic reagent, e.g. sodium hydroxide, sodium methoxide, sodium carbonate, or potassium hydroxide, provides the corresponding α-carbamoyl-β-cycloalkyl-β-oxopropionitrile. The general concept illustrated in Scheme 1 is applicable for the preparation of the α-alkanoyl derivatives by sustituting the starting β-keto ester with a 1,3-dione derivative [see for example, Ann. Chim. (Rome), 1965, 55:1233-41 (Chem. Abstr. 65:3853e, 1966)].

Scheme 2 shows an alternative procedure for the preparation of compounds of the present invention.

Scheme 3

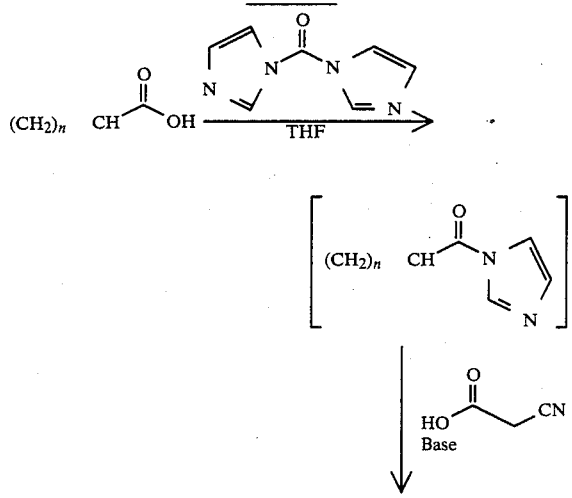

-continued
Scheme 3

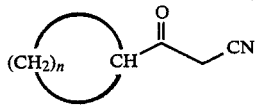

BIOLOGICAL ACTIVITY

Compounds of the present invention exhibit valuable pharmacological properties, in particular, anti-inflammatory and anti-arthritic activities. Representative compounds have been tested in the following in vivo models:

A. Modified Developing Adjuvant Arthritis in Rats

This test is based on the procedure originally described by Pearson (Proc. Soc. Biol. Med., 1956, pp 91-5). Each experimental group used six male Lewis rats weighing approx. 250 gm. Arthritis was produced by a single intradermal injection of *Mycobacterium butyricum* (0.6 mg in 0.1 ml mineral oil) into the base of the tail. Test compounds were administered orally, once daily, starting on the day of inoculation (day 1) through day 8. The initial dosage was reduced during this period when side effects were observed. The paw volume (average of two hind paws) was measured by the mercury displacement method at least twice weekly during the course of the experiment (40 to 42 days). The efficacy of a compound was expressed as the percent reduction of hind paw volume of treated vs. untreated rats using the following equation:

$$\% \text{ inhibition} = \frac{PC - RX}{PC - NC} \times 100$$

PC = positive control (not treated, arthritic)
NC = negative control (not treated, non-arthritic)
RX = drug group (treated, arthritic)

B. Carrageenin Induced Paw Edema in the Rat

This test is based on the procedure originally described by Holsapple and Yim (Inflammation, 1984, 8:223). Six male Sprague Dawley rats weighing approx. 300 gm were used in each experimental group. The rats had been starved for 24 hours prior to injection of 0.1 ml of 1% carrageenin into the plantar surface of the left hind paw. Test compounds were dosed orally 30 minutes prior to carrageenin administration. The volumes of the left hind paws were measured by mercury displacement at 2,4, and 6 hours following carrageenin injection. The efficacy of a compound was expressed as the percent inhibition of carrageenin injected paw volume as compared to non-injected paw using the following equation:

$$\text{Percent Inhibition} = \frac{C - RX}{C} \times 100$$

C = Vehicle control group (left paw volume − right paw volume)
RX = Drug treated group (left paw volume − right paw volume)

The peak of drug effects usually occurred 2-4 hours following carrageenin injection.

C. Delayed Type Hypersensitivity (DTH)

Male Lewis rats were immunized on Day 1. *Mycobacterium butyricum* in mineral oil (6 mg/ml) was injected into the base of the tail at 0.1 ml per rat. A negative control group receiving an equal amount of mineral oil was included. Drug therapy was administered orally from day one to day eight. Delayed type hypersensitivity was tested on day 9. Purified protein derivative (Tuberculin PPD, Statens Seruminstitute, Tuberculin Department, DK-2300 Copenhagen S, Denmark) was dissolved in phosphate buffered saline at 2.5 mg/ml. Twenty μl (50 μg) of the PPD solution was injected intradermally into the right ear of the rat, and the conralateral ear received 20 μl of the phosphate buffered saline vehicle. Forty-eight hours after injection the thickness of both ears was measured to the nearest 0.01 mm using a hand held caliper. The difference between the thickness of right and left ears was defined as the delta value for each rat. Group means and standard errors were compared using a Dunnett's 2-tail test.

Table I contains results of both modified developing adjuvant arthritis and carrageenin induced paw edema models.

TABLE I

Activities in adjuvant-induced polyarthritis (AIP) and carragenin-induced paw edema (CIP) models

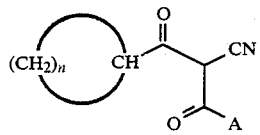

| Ex. # | Compound n = 2 | Dose (mg/kg)[a] | AIP Inhib. score[b] d. 20-22 | AIP Inhib. score[b] d. 40-42 | CIP[c] |
|---|---|---|---|---|---|
| 5 | A=CH3 | 95 (d. 1-2) 50 (d. 3-8) | ++ | ++ | I |
| 1 | NHCH3 | 100 | ++++ | ++++ | I |
| 2 | NHC(CH3)3 | 100 (d. 1-2) 50 (d. 3-8) | ++ | +++ | I |
| 8 | NHCH2CH=CH2 | 100 (d. 1-4) 50 (d. 5-8) | 0 | 0 | A |
| 4 | NHCH2C≡CH | 50 | +++ | +++ | A |
| 9 | NH—▷ | 100 (d. 1-3) | + | ++ | I |

TABLE I-continued
Activities in adjuvant-induced polyarthritis (AIP) and carragenin-induced paw edema (CIP) models

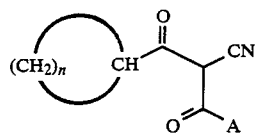

| | | | AIP | | |
|---|---|---|---|---|---|
| | Compound | | Inhib. score[b] | | |
| Ex. # | n = 2 | Dose (mg/kg)[a] | d. 20–22 | d. 40–42 | CIP[c] |
| | | 50 (d. 4) | | | |
| 6 | 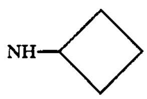  | 100 | + | + | I |
| 3 | $N(CH_3)_2$ | 100 | +++ | +++ | I |
| | n = 3 | | | | |
| 7 | A=$NHCH_3$ | 100 | 0 | + | I |

[a]once daily, p.o., from d. 1–8 (unless otherwise specified).
[b]% Inhibition of paw edema: 0 = <25; + = 25–<40; ++ = 40–<60; +++ = 60–<80; ++++ = 80–100.
[c]test compound administered as a single oral dose of 50 mg/kg 30 min. prior to carrageenin injection. % Inhibition determined 4 hrs. after carragenin injection; I = <25% reduction in paw volume and A = ≧25% reduction in paw volume.

Table II shows the effect of compound of Example 1 on the DTH response to *Mycobacterium butyricum* challenge in rats.

TABLE II
Effect of drug on delayed-type hypersensitivity (DTH) response

| Compound of | Dose mg/kg/d × 8 d.p.o. | % Reduction-DTH |
|---|---|---|
| Example 1 | 60 | 56 |
| | 30 | 41 |
| | 10 | 20 |

Compounds of the present invention show anti-inflammatory and/or anti-aarthritic activities in the animal models used. In addition, compound of Example 1 exhibits immunomodulating activity as evidenced by its ability to reduce delayed hypersensitivity in arthritic rats.

Compounds of the present invention may be formulated into pharmaceutical dosage forms suitable for administration via convenient routes such as oral, intravenous, intramuscular, subcutaneous, topical and intra-aricular. The formulated dosage forms may contain, in addition to the active agent, other pharmaceutically acceptable excipients to impart desirable pharmaceutical properties, for example, increased stability, improved taste, and improved appearance.

Compositions intended for oral administration may be in the form of tablets, pills, hard or soft gelaatin capsules, powders, elixirs, syrups, and suspensions. Tablets pills, powders and the like may contain additionally: a binder such as starch, gelatin, methylcellulose, or tragacanth; a disintegraant such as potato starch, alginic acid, or agar; a lubricant such as magnesium stearate, or polyethylene glycol; a diluent such as lactose, dextrose, mannitol, or cellulose; and/or other inert ingredients such as absorbants, colorants, flavoring agents, or sweeteners. Injectable compositions are preferably solutions or suspensions in a vehicle such as water, a pharmaceutically acceptable non-aqueous solvent, or a mixture thereof. They may contain, in addition to the active compound, preservatives (suchc as phenylmercuric nitrate, benzalkonum chloride, thimerosal, and benzyl alcohol), anaioxidants (such as sodium bisulfite and acetone sodium bisulfite), emulsifiers, or buffers (such as citrates, acetates and phosphates). For intravenous administration, the unit dosage form may be diluted with conventional IV fluids such as sterile Water for Injection, NaC1 Solution, or Ringer's Solution.

It will be appreciated that the actual preferred dosage of the compounds of the present invention will vary according to the particular compound being used, the particular formulation, mode of administration, and the severity of the disease being treated. Characteristics of the afflicted host such as sex, age, body weight, liver function, kidney function, and other concurrent drug therapies may also be considered by the attendign clinician. Optimal dosages for a given set of conditions can be ascertained by those skilled in the art using conventional dosage determination tests in view of the experimental animal data provided.

The following examples are illustrative of the present invention and are not to be construed as limiting its scope.

EXAMPLE 1

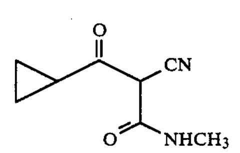

β-Cyclopropyl-β-oxo-α-methylcarbamoylpropionitrile

A. β-Cyclopropyl-β-oxopropionitrile

Cyclopropanecarboxylic acid (13.63 g, 0.15 mole) was added at 15° C. to a stirred solution of carbonyldiimidazole (24.36 g, 0.15 mole) in 300 ml of dry THF and the mixture waas stirred at ambient temperature for 2 h.

A solution of cyanoacetic acid (26.79 g, 0.315 mole) in 240 ml of methylene chloride plus 500 ml of dry THF was treated dropwise over 90 min with 315 ml of isopropylmagnesium chloride (2.0 M solution in THF) while maintaining the reaction temperature at <15° C. The white mixture was stirred at 23 ° C. for 2 h and to it was added, dropwise, the carbonyl imidazolide solution prepared above. Stirring was continued at room temperature for 17 h.

The reaction mixture was chilled in an ice bath and quenched by the cautious addition of 500 ml of 3 N HCl. The organic layer was removed at reduced pressure and the residue was extracted with several portions of either. The extracts were washed once with water, dried and evaporated to give a dark viscous liquid containing cyanoacetic acid. Distillation of the oil gave the ketonitrile as a near colorless liquid still contaminated with some cyanoacetic acid; bp 117°–139° C. (17 mm). Flash cchromatography of the crude product on silica agel using methylene chloride-Skellysolve B (85:15) as the eluant provided pure title compound that was distilled once again to a colorless oil. Yield: 12.20 g (75%); bp 124°–128° C. (21 mm).

Anal. Calcd for $C_6H_7NO$ : C, 66.04; H, 6.46; N, 12.83. Found: C, 65.60: H, 6.65; N, 12.77.

B.
β-Cyclopropyl-β-oxo-α-mehylcarbamoylpropionitrile

A solution of β-cyclopropyl-β-oxopropionitrile (3.50 g, 32.1 mmoles) [prepared in Step A]and triethylamine (TEA) (3.57 g, 35.3 mmoles) in 40 ml of toluene was treated at 20° C. with methyl isoccyanate (1.92 g, 33.7 mmoles) and the resultant solution was stirred at room temperataure for 17 h. The solvent was evaporated a reduced pressure and the syrupy residue, dissolved in 10 ml of methanol, was poured into a cold, stirred mixture of 100 ml water plus 5 ml 6 N HCl. The precipitate was collected by filtration and recrystallized from 90% aqueous ethanol to yield 4.18 g of the title compound, mp 130°–133° C.

Anal. Calcd for $C_8H_{10}N_2O_2$: C, 57.82; H, 6.06; N, 16.86. Found: C, 57.66; H, 6.08; N, 16.90.

EXAMPLE 2

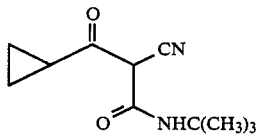

α-tert-Butylcaarbamoyl-β-cyclopropyl-β-oxopropionitrile

A. Ethyl β-cyclopropyl-α-ethoxymethylene-β-ketopropionate

Ethyl β-cyclopropyl-α-ketopropionate (247.0 g, 1.58 mole) [prepared according to the procedure described in J. Am. Chem. Soc., 70 , 497 (1948)], triethyl orthoformate (468.3 g, 3.16 mole) and acetic anhydride (484.0 g, 4.74 mole) were combined and the solution was stirred at reflux for 4 h and at ambient temperature for 17 h. The excess reagents were distilled at water aspirator pressure (maximum head temperature permitted was 72° C.) and the oily pot residue was stirred at 10° C. with a mixture of ether and water. The ether layer was separated, washed once with cold water and dried over $Na_2SO_4$. Removal of the solvent gave 321.5 g (96%) of an orange-red liquid that was used directly in the next step.

B. Ethyl 5-cyclopropylisoxazole-4-carboxylate

A mixture of hydroxylamine hydrochloride (105.0 g. 1.51 mole), ethyl β-cyclopropyl-α-ethoxymethylene-β-ketopropionate (320.0 g., 1.51 mole) [prepared in Step A], and 1200 ml of ethanol was refluxed for 2 h. The solvent was removed in vacuo and the residue was partitioned between water and ether. The organic phase was separated, washed again with water, dried and evaporated to leave a dark, greasy solid. Trituration of the crude product under Skellysolve B gave 158 g of the title compound.

A second crop of ester (50.0 g) was obtained by chromatographing the dark filtrate on 300 g of silica gel using first ca. 1 L of Skellysolve B-ether (95:5) followed by 3 L of Skellysolve B-ether (9:1). Total yield 76%. An analytical sample was prepared by recrystallizing an aliquot from a warm mixture of 10:1 Skellysolve B/ether, mp 52°–55° C.

Anal. Calcd for $C_9H_{11}NO_3$ : C, 59.66; H, 6.12; N, 7.73. Found: C, 59.72; H, 6.24; N, 7.62.

C. 5-Cyclopropylisoxazole-4-carboxylic acid

Ethyl 5-cyclopropylisoxazole-4-carboxylate (203.0 g, 1.12 mole) [prepared in Step B]was added to a solution of 405 ml of glacial acetic acid plus 505 ml of 6 N HCl and the mixture was heated in an oil bath a 105°–110° C. for 3 h. After 18 h at ambient temperature the thick mixture was diluted with water, cooled in an ice bath and filtered to give 140.8 g of the title acid. Recrystallization of an aliquot from acetonitrile gave an analytical sample, mp 163°–165° C.

Anal Calcd for $C_7H_7NO_3$ : C, 54.90; H, 4.60; N, 9.14. Found: C, 54.73; H, 4.51; N, 9.16.

D. 5-Cyclopropylisoxazole-4-carbonyl chloride

Thionyl chloride (195.8 g, 1.65 mole) was added dropwise to a stirred mixture of 5-cyclopropylisoxazole-4-carboxylic acid (140 g, 0.914 mole) [prepared above in Step C] and $Na_2CO_3$ (106.0 g, 1.0 mole) in 650 ml of chloroform. The mixture was heated at gentle reflux for 4 hr, then the solid was filtered and the filtrate evaporated to an oil. Distillation yielded 134.8 g of the acid chloride as a colorless liquid that readily crystallized to a low melting solid, bp 123°–125° C. (13 mm).

Anal. Calcd for $C_7H_6ClNO_2$: C, 49.00; 4, 3.52; N, 8.16. Found: C, 49.67; H, 3.80; N, 8.06.

E. 5-Cyclopropylisoxazole-4-(N-er-butyl)carboxamide

A solution of tert-butylamine (7.25 g, 99 mmoles) in 25 ml of methylene chloride was added dropwise at 10° C. to a solution of 5-cyclopropylisoxazole-4-carbonyl chloride (8.50 g, 49.5 mmoles) [prepared in Step D]in 100 ml of methylelne chloride and the reaction mixture was stirred at ambient temperature for 1 h. The mixture was then washed twice with water (6 HCl was added if necessary to make the washes acidic), dried and evaporated. The residual solid was recrystallized from Skellysolve B-ethyl acetate (4:1) to yield 6.71 g of the title compound as a white solid, mp 116°–118.5° C.

Anal. Calcd for $C_{11}H_{16}N_2O_2$: C, 63.44; H, 7.75; N, 13.45. Found: C, 63.28; H, 7.81; N, 13.45.

F.
α-tert-Butylcarbamoyl-β-cyclopropyl-β-oxopropioonitrile

Sodium hydroxide (33 ml of a 1.0 N solution) was added at 10° C. to a suspension of 5-cyclopropylisoxazole-4-(N-tert-butyl)carboxamide (6.83 g, 32.8 mmoles) [prepared in Step E]in 35 ml of water plus 5 ml of methanol and the mixture was stirred at room temperature until solution was complete. The cooled solution was then acidified with 6 N HCl and the precipitate was filtered. Recrystallization from 20% aqueous ethanol gave the title compound (5.23 g) as a white solid, mp 97°–98.5° C.

Anal. Calcd for $C_{11}H_{16}N_2O_2$ : C, 63.44; H, 7.75; N, 13.45. Found: C, 63.58; H, 8.01; N, 13.48.

EXAMPLE 3

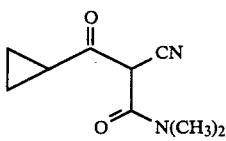

β-Cyclopropyl-α-dimethylcarbamoyl-β-oxopropionitrile

A.
5-Cyclopropylisoxazole-4-(N,N-dimethyl)carboxamide

A solution of 5-cyclopropylisoxazole-4-carbonyl chloride (8.0 g, 46.6 mmoles) [prepared in Example 2, Step D]in 80 ml of methylene chloride was reacted with a solution of dimethylamine (4.96 g, 0.11 mole) in 44.6 ml of methylene chloride according to the general procedure of Example 2, Step E. Distillation of an aliquot of the crude product gave the title compound as a colorless oil, bp 114°–116° C. (0.03 mm).

Anal. Calcd for $C_9H_{12}N_2O_2$ : C, 59.98; H, 6.71; N, 15.55. Found: C, 60.09; H, 7.02; N, 15.46.

B.
β-Cyclopropyl-α-dimethylcarbamoyl-β-oxpropionitrile

The product from Step A above (4.0 g, 22.2 mmoles) in a mixture of 40 ml of water plus 5 ml of methanol was treated at 10° C. with 23 ml of 1.0 N sodium hydroxide and the mixture was stirred at room temperature for 90 min. The resulting solution was cooled, acidified with 6 N HCl and the precipitate filtered. Recrystallization from 45% aqueous ethanol yielded 3.08 g of the title compound, mp 44.5°–46° C.

Anal. Calcd for $C_9H_{12}N_2Ohd 2$ : C,59.98; H, 6.71; N, 15.55. Found: C, 59.88; H, 6.93; N, 15.60.

EXAMPLE 4

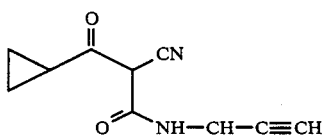

β-Cyclopropyl-β-oxo-α-propargylcarbamoylpropionitrile

A.
5-Cyclopropylisoxazole-4-N-(propargyl)carboxamide

The general procedure of Example 1, Step E was repeated, except that the tert-butylamine utilized therein was replaced with two equivalents of 2-propynylamine. The crude product was placed on 65 g of silica gel and chromatographed using first methylene chloride followed by methylene chloridemethanol (98:2). This yielded 76% of the title compound that was recrystallized from ethyl acetate/Skellysolve B, mp 83°–85.5° C.

Anal. Calcd for $C_{10}H_{10}N_2O_2$ : C, 63.14; H, 5.30; N, 14.73. Found: C, 63.42; H, 5.39; N, 14.86.

B.
β-Cyclopropyl-β-oxo-α-propargylcarbamoylpropionitrile

A suspension of 5-cyclopropyl-4-N-(2-propynyl)-carboxamide (2.12 g, 11.1 mmoles)[prepared in Step A]in 15 ml of water plus 5 ml of methanol was treated at 10° C. with 12.5 ml of 1.0 N NaOH and he mixture was stirred at ambient temperature until solution was observed. The solution was then cooled, acidified with 6 N HCl and the product collected by filtration. Recrystallization from 40% aqueous acetonitrile gave the title compound (1.72 g) as a white solid, m.p. 127.5°–129° C.

Anal. Calcd for $C_{10}H_{10}N_2O_2$ : C, 63.14; H, 5.30; N, 14.73. Found: C, 62.79; H, 5.37; N, 14.80.

EXAMPLE 5

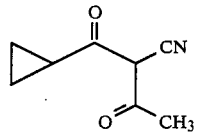

α-Acetyl-β-cyclopropyl-β-oxopropionitrile n-Buyllithium (19.44 ml, 52.5 mmole of a 2.7 M solution in hexane) was added at -15° C. to a solution of diisopropylalmine (5.31g, 52.5 mmole) in 80 ml of dry THF. After 10 min the cooling bath was lowered to −70° C. and 5-methylisoxazole (4.15 g, 50 mmoles) was added to the lithium diidopropylalmine (LDA) solution followed in 30 min by the dropwise addition of cyclopropanecarboxylic acid chloride (5.33 g, 50 mmoles) in 15 ml of THF. The reaction mixture was then stirred at −78° C. for 30 min and at ambient temperature for 2 h. The solvents were evaporated and the residue was partitioned between ether, 30 ml of water and 13 ml of 4 N NaOH. The aqueous layer was separated, acidified with 6 N HCl and extracted with two portions of ether. The extracts were dried and evaporated to a slushy solid that was cchromatographed on 100 g of silica gel using methylene chloride-Skellysolve B (95:5). The appropriate fractions were combined and concentrated to yield 2.26 g of the title compound as a yellow-tinted solid, mp 62°–63.5° C.

Anal. Calcd for $C_8H_9NO_2$ :C, 63.57; H, 6.00; N, 9.27. Found: C, 63.48; H, 6.01; N, 9.13.

EXAMPLE 6

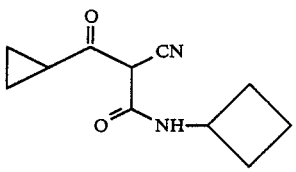

α-Cyclobutylcarbamoyl-β-cyclopropyl-β-oxopropionitrile

A.
5-Cyclopropylisoxazole-4-(N-cyclobutyl)carboxamide

The general procedure of Example 2, Step E was repeated, except that the tert-butylamine utilized therein was replaced with one equivalent each of cyclobutylamine and diisopropylethylamine. The crude oil was placed on 70 g of silica gel and chromatographed using methylene chloride followed by methylene chloride containing 2% methanol. The appropriate fractions were combined and evaporated to give a waxy solid. Recrystallization from ethyl acetate/Skellysolve B yielded 39% of the title compound, mp 103°–105° C.

Anal. calcd for $C_{11}H_{14}N_2O_2$ : C,64.06; H, 6.84; N, 13.59. Found: C, 64.17; H, 7.01; N, 13.57.

B.
α-Cyclobutylcarbamoyl-β-cyclopropyl-β-oxopropionitrile

A suspension of 5-cyclopropylisoxazole-4-(N-cyclobutyl)carboxamide (3.10 g, 15 mmoles) [prepared in Step A]in 15 ml of water plus 5 ml of methanol was treated at 0° C. with 16 ml of 1.0 N NaOH and the mixture was stirred at ambient temperature until solution was observed. The solution was then cooled, acidified with 6 N HCl and he product collected by filtration. Recrystallization from 30% aqueous ethanol yielded 1.86 g of the title compound as a white solid, mp 110°–111° C.

Anal. Calcd for $C_{11}H_{14}N_2O_2$ : C,64.06; H, 6.84; N, 13.59. Found: C, 63.68; H, 7.04; N, 13.43.

EXAMPLE 7

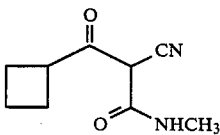

β-Cyclobutyl-β-oxo-α-methylcarbamoylpropionitrile

A. β-Cyclobutyl-β-oxopropionitrile

The general procedure of Example 1, Step A was repeated, except that athe cyclopropanecarboxylic acid utilized therein was replaced with an equivalent amount of cyclobutanecarboxylic acid. After workup, purification by chromatography on silica gel and distillation, the title compound was obtained as a yellow-tinted liquid, bp 118°–121° C. (11 mm).

Anal. Calcd for $C_7H_9NO$ : C, 68.27; H, 7.37; N, 11.37. Found: C, 68.02; H, 7.63; N, 11.12.

B.
β-Cyclobutyl-β-oxo-α-methylcarbamoylpropionitrile

β-Cyclobutyl-β-oxopropionitrile (2.25 g, 18.3 mmoles) [prepared in Step A]was reacted with methyl isocyanate (1.10 g, 19.2 mmoles) according to the general procedure of Example 1, Step B to yield 2.57 g of the title compound as a white solid afater recrysstallization from 50% aqueous ethanol, mp 81°–83° C.

Anal. Calcd for $C_9H_{12}N_2O_2$ : C, 59.98; H, 6.71; N, 15.55. Found: C, 60.17; H. 6.71; N. 15.52.

EXAMPLE 8

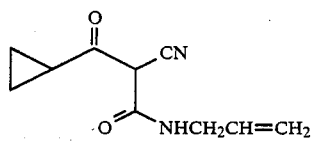

α-Allylcarbamoyl-β-cyclopropyl-β-oxopropionitrile

When β-cyclopropyl-β-oxopropionitrile (2,.00 g, 18.3 mmoles) [prepared in Example 1, Step A]was reacted with allylisocyanate (1.60 g, 19.2 mmoles) according to the general procedure of Example 1, Sep B, the title compound (2.8 g) was obtained as a white solid after recrystallization from 30% aqueous ethanol, m.p. 72°–73.5° C.

Anal. Calcd for $C_{10}H_{12}N_2O_2$ : C, 62.48; H, 6.29, N, 14.58. Found: C, 62.70; H, 6.32; N, 14.60.

EXAMPLE 9

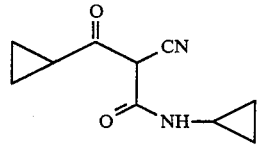

α-Cyclopropylcarbamoyl-β-cyclopropyl-β-oxopropionitrile

A.
5-Cyclopropylisoxazole-4-(N-cyclopropyl)carboxamide

The general procedure of Example 2, Step E was repeated, except that two equivalents of tert-butylamine utilized therein were replaced with one equivalent of cyclopropylamine and one equivalent of diisopropylethylalmine. The crude product was purified by flash chromatography using methylene chloride followed by methylene chloride-methanol (98:2) and then recrystallized from ethyl acetate-Skellysolve B to yield 76% of the title compound, mp 102°–105° C.

Anal. Calc. for $C_{10}H_{12}N_2O_2$: C, 62.48; H, 6.29; N, 14.58. Found: C, 62.19; H, 6.36; N, 14.55.

B.
α-Cyclopropylcarbamoyl-β-cyclopropyl-β-oxopropionitrile

The general procedure described in Example 6, Step B was followed except 5-cyclopropyylisoxazole-4-(N-cyclopropyl) carboxamide was used in place of the N-cyclobutyl analog used therein to provide the title compound as a white solid, m.p. 136°–138.5° C.

EXAMPLE 10

The general procedure described in Example 2, Step E was repeated except tert-butylamine used therein was replaced by methlamine to provide 5-cyclopropylisoxazole-4-(N-methyl)-carboxamide, m.p. 77°–80° C. he isoxazole thus obtained may be subjected to treatment with NaOH using the procedue of Example 2, Step F to provide the product of Example 1.

What is claimed is:

1. A compound having the formula

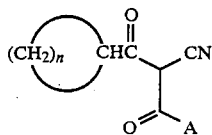

wherein
$n = 2, 3, 4,$ or 5;
A is $C_{1-5}$alkyl, $NHR^1$, or $NR^2R^3$; wherein $R^1$ is selected from the group consisting of $C_{1-5}$alkyl, $C_{2-5}$alkenyl, $C_{2-5}$alkynyl, and $C_{3-6}$cycloalkyl with the proviso that when n is 2, $R^1$ is not ethyl or isopropyl; and $R^2$ and $R^3$ are the same or different $C_{1-5}$alkyl;
or a pharmaceutically acceptable salt thereof.

2. The compound of claim 1 wherein A is $C_{1-5}$alkyl.

3. The compound of claim 2 wherein n is 2 and A is methyl.

4. The comound of claim 1 wherein A is $NHR^1$.

5. The compound of claim 4 wherein n is 2.

6. The compound of claim 5 wherein $R^1$ is selected from the group consisting of methyl, $C_{4-5}$alkyl, $C_{3-5}$alkenyl, $C_{3-5}$alkynyl, and $C_{3-4}$cycloalkyl.

7. The compound of claim 6 wherein $R^1$ is methyl.

8. The compound of claim 6 wherein $R^1$ is tert-butyl.

9. The compound of claim 6 wherein $R^1$ is propargyl.

10. The compound of claim 6 wherein $R^1$ is allyl.

11. The compound of claim 6 wherein $R^1$ is cyclobutyl.

12. The compound of claim 6 wherein $R^1$ is cyclopropyl.

13. The compound of claim 4 wherein n is 3, 4, or 5.

14. The compound of claim 13 wherein n is 3 and $R^1$ is methyl.

15. The compound of claim 1 wherein A is $NR^2R^3$.

16. The compound of claim 1 wherein $R^2$ and $R^3$ are each methyl and n is 2.

17. A pharmaceutical composition comprising a therapeutically-effective amount of a compound of claim 1 and a pharmaceutically acceptable carrier.

18. A method for treating a mammalian host suffering from arthritic condition which comprises administering to said host an anti-arthritic effective dose of a compound of claim 1.

19. A method for treating a mammalian host suffering from inflammation condition which comprises administering to said host an anti-inflammatory effective dose of a compound of claim 1.

* * * * *